US00PP09970P

United States Patent [19]

Hofmann

[11] Patent Number: Plant 9,970

[45] Date of Patent: Jul. 15, 1997

[54] VARIETY OF GERANIUM NAMED 'PENVE'

[75] Inventor: Christa Hofmann, Grossdittmannsdorf, Germany

[73] Assignee: Elsner Pac Jungpflanzen, Germany

[21] Appl. No.: 536,658

[22] Filed: Sep. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Webb Ziesenheim Bruening Logsdon Orkin & Hanson, P.C.

[57] ABSTRACT

The new cultivar has a leading bright violet flower with great luminosity. It has a compact round growth habit and zoned leaves. It flowers continuously during the summer, beautiful in all weather and exhibits a very good garden performance. This mass-propagation variety is early to flower with very big umbels and produces an economical, high cutting yield without problems. It is suitable for all purposes, such as for early selling as potted plants, for use in window boxes or as bedding plants. The new cultivar is an improvement in comparison to the old violet variety "PAC Rospen".

1 Drawing Sheet

BACKGROUND OF THE INVENTION

The present invention comprises a new and distinct cultivar of *Pelargonium×hortorum* known by the varietal name 'Penve'. The new variety was discovered at Elsner pac Jungpflanzen in Dresden, Germany in May, 1988. The new variety was discovered by crossbreeding several breeding lines, which are unnamed, but which are maintained proprietary for breeding purposes. The new variety was first asexually reproduced by cuttings at Elsner pac Jungflanzen in Dresden, Germany in October, 1988. It has also been trial and field tested from the year after discovery up to now at Elsner pac Jungpflanzen in Dresden, Germany and has been found to retain its distinctive characteristics through successive propagations.

The plant history was taken on six week plants blossomed under the natural light in a green house in 12 cm pots. The cultivar when grown in a glass greenhouse was potted on the Feb. 17, 1995 and flowered on Mar. 30, 1995.

DESCRIPTION OF THE DRAWING

The accompanying photographic drqwing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Elsner pac Jungpflanzen in Dresden, Germany. The plant history was taken on six week plants blossomed under natural light in a greenhouse and the color readings were taken indoors under natural light in a room near a window without direct sunlight. Color references are primarily to The R.H.S. Color Chart of The Royal Horticultural Society of London.

THE PLANT

Classification:

*Botanical.*—*Pelargonium×hortorum.*

*Commercial.*—Zonal florists' geranium.

*Form.*—Compact mound form with a dense canopy.

*Height.*—16.0–18.0 cm.

*Growth.*—Free and early flowering, basal branching.

*Strength.*—Stands upright without artificial support. More tolerant than other plants of this market class to the vagaries of weather.

*Foliage.*—Stalked leaf attachment, zone present.

Leaves:

*Size.*—Length: 4.8–6.0 cm. Width: 8.0–9.0 cm.

*Shape.*—Reniform, cordate base.

*Margin.*—Crenate.

*Texture.*—Pubescent.

*Color.*—Top: Green Group 147B; Bottom: Green Group 138B; Zone: Green Group 147A.

Ribs and veins:

*Venation type.*—Palmate.

*Color.*—Green Group 138B.

Petioles:

*Color.*—Green Group 143C.

*Length.*—5.5–6.5 cm.

Stem:

*Color.*—Yellow-Green Group 145B.

*Internodes.*—2.0–3.0 cm in length.

THE BUD

Shape: Upright hemispherical clusters.

Size (diameter): 2.5–3.0 cm. just prior to unfolding of the petals.

INFLORESCENCE

Blooming habit: Free and early flowering, semi-double, not shattering.

Size (diameter): 10.0–12.0 cm, fully open umbel.

Borne: Umbel, florets on pedicel, pedicel on peduncle, flowers above the foliage.

Umbels:

*Number.*—10.

*Number of florets per umbel.*—15.

*Blooming.*—Constant numbers of florets over growing season.

*Pinching.*—None necessary to obtain branching or repeated blooming. No seed formation if spent umbels not pinched; plant forms new umbels and flowers.

Florets:

*Form.*—Semi-double, flat to slightly cupped.

*Color.*—Top: Red-Purple Group 67B; Red-Purple Group 65A on the lower part of the petal with veins at Red-Purple Group 68A. Bottom: Red-Purple Group 67B.

*Size.*—4.5–5.0 cm in diameter.

Petals:

*Shape.*—6–8, overlapping, ovate.

*Margin.*—Entire.

*Texture.*—Smooth.

*Size.*—2.2 cm long, 2.2 cm wide.

*Texture and appearance.*—Petals are smooth, slightly reflective, and have an unusually high degree of luminescence. They present a starkly contrasting and dramatically attractive, eye catching splash of luminescent violet above the zoned leaves (zonation not visible in the photograph).

Petaloids:

*Quantity.*—2–3.

*Size.*—1.5 cm long, 0.3 cm wide to 1.9 cm long, 0.7 cm wide.

*Shape.*—Single based, with ends split to 1–3 points, points twisted.

*Color.*—Like the petals.

Calyx:

*Form.*—Cup shaped.

*Color.*—Yellow-Green Group 144B with Greyed-Purple Group 185B on lower part.

*Sepal size.*—1.0–1.2 cm long, 0.2–0.4 cm wide.

*Sepal shape.*—Lanceolate.

Pedicel:

*Length.*—2.5–2.8 cm.

*Color.*—Greyed-Purple Group 185B.

Peduncle:

*Color.*—Yellow-Green Group 152A.

*Length.*—13.0–17.0 cm.

Disease resistance: Apparently high resistant to common diseases of plants of this market class because no unusual susceptibilities have been observed in the culture of this plant.

Lasting quality: Very long.

REPRODUCTIVE ORGANS

Stamens:

*Number.*—8.

*Anthers.*—1.5–2.0 mm in length.

*Filaments.*—Length: 7.0 mm. Color: Pink.

*Pollen.*—Golden brown.

Pistils:

*Number.*—1.

*Length.*—9.0 mm.

*Stigma.*—Number: 1, 5–6 parted. Color: Red Purple.

*Style.*—Length: 4.0 mm. Color: Red Purple.

Ovaries:

*Pubescence.*—Superior, pubescent.

*Length.*—4.0 mm.

*Width.*—2.5 mm.

*Color.*—Green.

Fruit: None observed.

*Fecundity.*—Pollen is formed. No seed setting during normal growing as balcony and bedding plant. Seed setting observed after hard pollination.

Seed formation: None during normal growing.

GENERAL CHARACTERISTICS

1. Leading bright violet flowering variety with great luminosity.

2. Compact round growth habit, zoned leaves.

3. Continuous flowering during the summer.

4. Early flowering, very big umbels.

5. Economic production, high cutting yield.

6. Mass-propagation variety without problems.

7. Beautiful in all weathers.

8. Very good garden performance.

9. Suitable for all purposes: early selling as pot plant, use in window-boxes or as bedding plant.

10. Essential improvement in comparison with the old violet variety "PAC Rospen".

I claim:

1. A new and distinct variety of geranium plant substantially as shown and described.

* * * * *

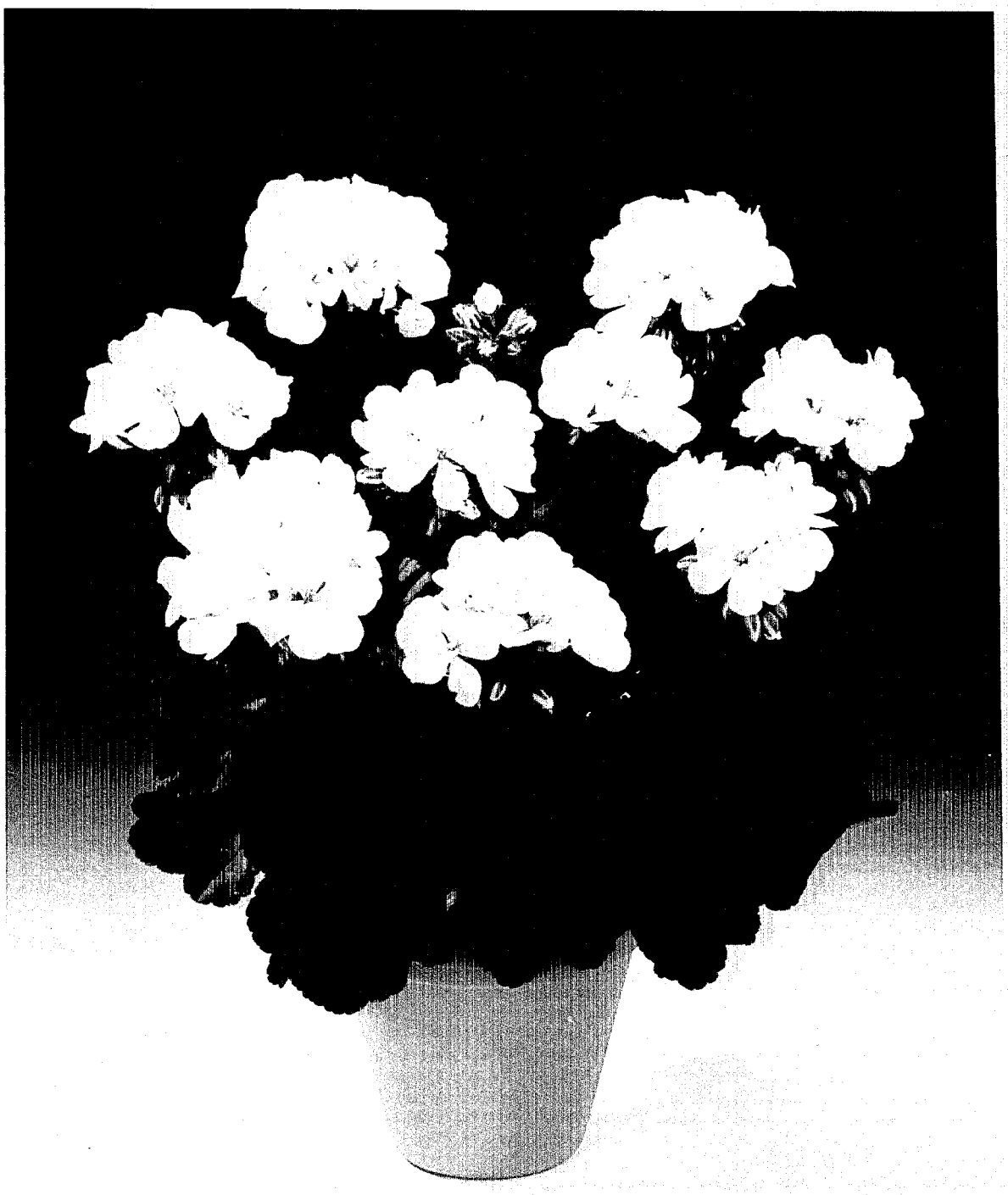

UNITED STATES PATENT AND TRADEMARK OFFICE

CERTIFICATE OF CORRECTION

PATENT NO. : Plant 9,970

DATED : July 15, 1997

INVENTOR(S) : Christa Hofmann

It is certified that error appears in the above-identified patent and that said Letters Patent is hereby corrected as shown below:

The drawing in Patent No. Plant 9,970 should be in Patent No. Plant 9,971.

The drawing in Patent No. Plant 9,971 should be in Patent No. Plant 9,970.

Signed and Sealed this

Thirteenth Day of January, 1998

Bruce Lehman

*Attest:*

BRUCE LEHMAN

*Attesting Officer*

*Commissioner of Patents and Trademarks*